(12) United States Patent
Sidebotham (10) Patent No.: US 8,454,665 B2
(45) Date of Patent: Jun. 4, 2013

(54) MULTI-PURPOSE BONE PLATE SYSTEM

(76) Inventor: Christopher G. Sidebotham, Mendham, NJ (US)

( * ) Notice: Subject to any disclaimer, the term of this patent is extended or adjusted under 35 U.S.C. 154(b) by 786 days.

(21) Appl. No.: 11/228,807

(22) Filed: Sep. 16, 2005

(65) Prior Publication Data

US 2007/0083204 A1   Apr. 12, 2007

(51) Int. Cl.
*A61B 17/80*   (2006.01)

(52) U.S. Cl.
USPC .......................................... 606/280; 606/915

(58) Field of Classification Search
USPC ............................. 606/69–71, 283, 284, 285
See application file for complete search history.

(56) References Cited

U.S. PATENT DOCUMENTS

| | | | |
|---|---|---|---|
| 2,737,835 A | 3/1956 | Herz | 81/15 |
| 3,866,458 A | 2/1975 | Wagner | 72/459 |
| 3,965,720 A | 6/1976 | Goodwin et al. | 72/458 |
| 5,113,685 A | 5/1992 | Asher et al. | 72/458 |
| 5,564,302 A | 10/1996 | Watrous | 72/458 |
| 5,746,742 A | 5/1998 | Runciman et al. | 606/69 |
| 5,904,684 A | 5/1999 | Rooks | 606/69 |
| 5,968,047 A | 10/1999 | Reed | 606/76 |
| 6,077,271 A | 6/2000 | Huebner et al. | 606/101 |
| 6,283,969 B1 * | 9/2001 | Grusin et al. | 606/280 |
| 6,712,073 B2 | 3/2004 | Manderson | 128/898 |
| 7,771,457 B2 * | 8/2010 | Kay et al. | 606/284 |
| 2003/0055435 A1 | 3/2003 | Barrick | 606/102 |
| 2004/0019353 A1* | 1/2004 | Freid et al. | 606/69 |
| 2004/0116934 A1 | 6/2004 | Capanni | 606/86 |

FOREIGN PATENT DOCUMENTS

| DE | 3724479 | 2/1989 |
|---|---|---|
| DE | 3839859 | 8/1989 |
| EP | 1132052 | 9/2001 |

* cited by examiner

*Primary Examiner* — Eduardo C Robert
*Assistant Examiner* — Jerry Cumberledge
(74) *Attorney, Agent, or Firm* — Ernest D. Buff; Ernest D. Buff & Assoc LLC; Harry Anagnos (57) ABSTRACT

A multi-purpose bone plate system comprises a set of sterile malleable bone plates, an adjustable bending and contouring tower with adjustable angulation and compression slots and a set of bone plates with angulation and compression slots positioned at pre-selected locations to aid three-dimensional shaping of the bone plate. The surgeon inserts the sterile bone plate template to surround the fractured bone and works the template to acquire the physical shape of the fractured bone, inserts the template into the tower to set the adjustable angulation and compression slots of the tower. Now a symmetrical bone plate is inserted into the tower and bent to a shape that replicates the shape of the bone plate. The three-dimensionally shaped bone plate is sterilized and is attached by screws or nails surrounding the fractured bone segment and provides support to fractured bone segments during healing of the bone.

11 Claims, 5 Drawing Sheets

Fig. 1a 2.7 mm Plate          3.5 mm Plate

Tibial Plateau Leveling Osteotomy

Ilial Shaft Fracture

Partial Carpal Arthrodeis

MULTI-PURPOSE BONE PLATE SYSTEM

BACKGROUND OF THE INVENTION

1. Field of the Invention

The present invention relates to a bone plate system and apparatus for bending bone plates; and more particularly, to a system that comprises readily formable bone plates and a bending and configuring tower designed to create a bone plate shape that matches a template.

2. Description of the Prior Art

Many patents address issues related to bone plates and apparatus for bending bone plates. Some of the patents relate to bone plates for human use while others relate to bone plates for canine use.

U.S. Pat. No. 2,737,835 to Herz discloses tools for bonding plates in bone surgery. A flat plate is bent at a suitable location using a bending tool. As shown above in FIG. 4, three Smith-Petersen nails are inserted in one of the broken femur bones and a fourth nail is inserted into the femoral shaft to rigidly hold the broken bones in place without movement, to promote bone healing. The plate used is a two-dimensional object. It does not completely support the three dimensional bone segments that have fractured; but relies on the nails to prevent movement of the bone plate.

U.S. Pat. No. 3,866,458 to Wagner discloses a bender for contouring surgical implants. The bender has a pair of bending tools, one of which is specifically adapted for use in bending a particular hip fixation plate and the other of which is adaptable for use on bending a wide variety of metallic surgical implants including a hip fixation plate. The first of the benders has an elongated handle portion conforming to the femur shaft and a flat bowl-shaped head portion conforming to the lower portion of the greater trochanter of a femur. The head portion has at least one transversing bore for receiving a hip screw. The first bender is designed to grip the head portion of the plate. It has an upper jaw and a lower jaw pivotally interconnected at one end. A swing bolt and wing nut are disposed on the other end. The inner surface of one of the jaws has one or more nipples for registering with transverse bores of the head portion. The inner surface of the other jaw is adapted to close against the side of the head portion facing it. An elongated handle is rigidly attached to the bottom of the lower jaw for gripping purposes. The second bender may be used to grip any generally flat implant having opposed sides. It has a housing with a channel extending longitudinally through it. One side of the channel is contoured to conform to the contour of one of the opposed sides of the implant. A jaw member is disposed within the channel. The jaw member is adapted for vertical movement, which raises and lowers the jaw member within the channel. An elongated handle extends from the housing for gripping purposes. The second bender is used by sliding the implant into the channel in the space between its one side and the jaw member. The jaw member is raised until the implant is clamped between it and one side of the channel. The bone plate disclosed by the '458 patent is clearly not suitable for multiple purposes.

U.S. Pat. No. 3,965,720 to Goodwm et al. discloses a hinge adjustment tool. This hinge adjustment tool is designed for use on self-closing hinges for kitchen cabinets. The hinge has the form of a bar of hot rolled steel. End portions of the bar are displaced out of the plane of the bar's intermediate portion. Such displacement is produced in opposite directions at an angle of about 45° by a cold bending operation. The end portions are provided with a slot opening facing in opposite directions, and with the end portions of the hinge tool hardened by heat treatment. This hinge is designed for self-closing kitchen cabinets. The ends of the hinge bar are bent in opposite directions, and are provided with slots facing the opposite direction. This hinge adjustment tool has a structure and function distinctly different from a multi-purpose bone plate for orthopedic applications.

U.S. Pat. No. 5,113,685 to Asher et al. discloses an apparatus for contouring spine plates and/or rods. A plurality of instruments or members plastically deform spine plates or rods to a configuration, which corresponds to a desired configuration for connection to a spinal column. A pair of flat benders having slots are engageable with a spine plate to bend and/or twist the spine plate. A pair of tube benders is engageable with a rod to bend the rod. One of the flat benders may be used with one of the tube benders to form a bend in the rod. In addition, the two flat benders may be used together to bend the rod. These instruments make possible two-dimensional bending of spine plates and three-dimensional bending of spine rods. The spinal plate disclosed by the '685 patent is not a bone plate. It is not used to fix broken bone; but rather keeps the spinal column in a desired position.

U.S. Pat. No. 5,564,302 to Watrous discloses orthopedic bone plate bending irons. The orthopedic bone plate bending irons comprise a simple machine that permits the application of a concentrated bending moment to a stiff metallic bone plate. The bends are accomplished along three orthogonal torsional axes, enabling a modest sized operator to bend the most stout bone plates. The bending moments are transmitted to the bone plates through the edges of curved apertures, so that the built in transverse curvature of the plate is not crushed with resulting weakening of the plate. Finally, the apertures are rotated and angled to provide comfortable hand clearance and to permit efficient application of muscle force by the operator. The bone plate is inserted into angled slots in a pair of irons and the distal end of the irons is moved to bend the bone plate. The bending action only bends the overall plate and portions of the plate cannot be contoured to fit a three-dimensional fractured bone. There is no template provided to adjust bending and twisting in accordance with surgical requirements.

U.S. Pat. No. 5,746,742 to Runciman et al. discloses a bone plate template. This bone plate template is composed of 1100-0 aluminum. It comprises reduced width connecting sections that have a width to thickness ratio of 1.6:1 to 1.4:1, so that these connecting sections may be manually bent or twisted without forming folds or kinks. The template disclosed by the '742 patent is not a template for a symmetrical bone plate; it cannot be used in both left handed and right-handed conditions. After the bone plate template is bent to desired shape, the actual bone plate must be bent by application of a large amount of force. This procedure causes the bone plate template with the desired shape to be bent out of shape during the bending operation of the actual bone plate. The template disclosed by the '742 patent is only a template; and provides no disclosure for bending a bone plate.

U.S. Pat. No. 5,904,684 to Rooks discloses a device and method for simultaneous bilateral pelvic osteotomies. This method and device facilitates the procedure of a transverse osteotomy of both ilium and a secondary osteotomy through the pelvic symphysis. A plate is utilized which has facility for attachment of eight screws into the, animal bone tissue to more securely hold the plate in place. The shape of the plate represents a significant advance and has important characteristics. Only one side of the plate has sharply angled surfaces to accommodate rotated pelvic bone portions, while the other side of the plate is smooth and facilitates a more stable direct insertion of the bone screws. In this configuration, the bores can closely match the shapes of the heads of the bone screws and provide less exposed material at the outside of the plate. The plate is adapted to be bent. More than ample material is provided to bend the plate along its axis to facilitate insertion of bone screws at right angles to the extent of the pelvic bone tissue. The bone plate has two wedge shaped elements, which are twisted and bent according to surgical requirements. It is not symmetrical, and cannot be interchangeably used for the left side and right side before bending. The bone plate is made of solid metal and cannot be easily bent into three-dimensional shapes.

U.S. Pat. No. 5,968,047 to Reed discloses a fixation device. A sterile bone fixation device in the form of a screw, pin or bone plate is made from sterile animal or human bone. Perforations are provided on the surface for improved bone bonding. The bone plate disclosed by the '047 patent is not bendable, and cannot be easily shaped to conform to the three dimensionality of a fractured bone.

U.S. Pat. No. 6,077,271 to Huebner et al. discloses a bone plate vise. The vise is provided as an aid in bending a bone plate. The vise includes an elongate handle and a first clamp mechanism. The clamp mechanism includes a plate-receiving slot having an axis perpendicular to the long axis of the handle and rotationally fixed to the handle. The clamp mechanism also includes a moveable jaw bordering the plate-receiving slot. A jaw tightening mechanism urges the moveable jaw against a bone plate positioned in the plate-receiving slot to thereby secure the plate in the vise. The bone plate is inserted into the vice and is clamped securely. The free end of the bone plate is bent or twisted using a bending iron. There are no provisions to control the location of the bend or twist or the amount of bend or twist. Since the wider portion of the bone plate is within the bone vice, it cannot be contoured to conform to the three dimensional shape of a bone.

U.S. Pat. No. 6,712,073 to Manderson discloses an extramedullary rod implant for long bones. A method for inserting a solid rod implant into the body is detailed by the '073 patent. The implant is designed for bridging two portions of a broken long bone, and maintaining the divided portions of the bone in stable alignment with each other. The solid rod implant is rigidly attached to the damaged long bone by a pair of partly tubular plates at either end of the rod. These plates provide the sole means of attachment of the implant to the bone. That is, there is no provision for any attachments along, beside or through any portion of the rod that would allow it to be attached to any portion of the bone providing support for osteosynthesis. By its design and method of rigid attachment to the bone through partly tubular end plates, the implant allows controlled motion at the fractured or nonunited portions of the bone fragments. This motion stimulates rapidly forming external bridging callus formation for osteosynthesis of the long bone, a process that shortens the time of osteosynthesis of long bones so treated. This long implant is attached further from the bone fracture region using screws. The arrangement allows gentle movement at the fracture, which is said to promote the healing process. The shape of the implant rod and the attachment points are not contoured three dimensionally according to the shape of the bone. In fact, the fractured portion of the bone is not surgically disturbed and the implant is not set against the fractured bone.

U.S. Patent Application No. 2003/0055435 to Barrick discloses an orthopedic implant shaper. This implant shaper system consists of a flexible fiber optic curvature sensor device, a computer, and an implant-shaping machine. The flexible fiber optic curvature sensor device is a tape used to determine the required three-dimensional shape of an orthopaedic implant. The sterilized tape is applied to the fractured bone in surgery once it is reduced. The shapes and sizes of various metal orthopaedic implants are stored on the hard disc of the computer in a lookup table file. The operator inputs the type of implant to be contoured and the number of holes of a plate or length of a rod. The digitized contour of the tape is then matched with the particular bone implant. The information is transmitted to the implant-shaping machine to program the settings for the actual contouring. The implant-shaping machine consists of a series of opposing hydraulic cylinders with dies arranged in rows on rocking platforms. Each unit consists of a pair of opposing hydraulic cylinders that work reciprocally to move dies in relation to the metal fixation implant. In this invention, a fiber optic tape curvature sensor is placed on a bone that is fractured. The fiber optic tape is illuminated; the curvature of the tape placed on the bone is detected; and the information is sent to a computer, which controls implant-shaping machine. The implant is a machined device matching the exact dimension of bone curvature as detected by a fiber optic sensor tape. The strength of the implant, its biocompatibility and its means of attachment to fractured bone is not disclosed.

U.S. Patent Application No. 2004/0116934 discloses a tool system for adapting a bone plate. The tool system is for working on a bone plate and includes a first tool and a second tool. Both tools are used at the same time to shorten or bend the bone plate. The tool system for adapting bone plates is provided with a first tool having a first and a second introduction opening for bone plates, and a second tool having a third and a fourth introduction opening for bone plates. For cutting the bone plate, the bone plate is arranged in the first and third introduction openings, and for bending it is arranged in the second and fourth introduction openings. One or more of the introduction openings may be of closable construction in order to enable a bone plate which is to be worked on to be received such that it cannot come free. The two tools are used at the same time when shortening or bending the bone plate. This tool has an opening for cutting or shortening a bone plate and openings for bending the bone plate. The bone plate can only be cut at the ends of the bone plate and the bending movement is possible with the ends clamped by the tool. The precise location of the bend in the bone plate cannot be adjusted. The bone plate disclosed by the '934 application cannot be bent to a three-dimensional shape.

There remains a need in the art for a method and means for three dimensionally bending bone plates to provide three-dimensional support to fractured bone segments, thereby retaining the surgeon-set position of the bones during the bone-healing period. There is also a need for shaped bone plates that are suited for canine use; which can accommodate the small size of canine bone segments; which can be implanted so that the mobility of the operated animal is maintained immediately after surgery. Further needed is a bone plate system that provides intimate contact between fractured bone segments during the healing period, so that a long-term permanent bond between the implant and the underlying bone structure is made possible and extended motion meeting the canine needs can be achieved. Still further there is needed a bone plate system wherein the implanted bone plate is not removed during the remaining lifetime of the dog, and continues to function flawlessly without corrosion or rejection reactions throughout its service life.

SUMMARY OF THE INVENTION

The present invention provides a method and means for three dimensionally bending bone plates to provide three-dimensional support to fractured bone segments, thereby retaining the surgeon-set position of the bones during the bone-healing period. Shaped bone plates provided in accordance with the present invention are especially suited for canine use. Such bone plates can accommodate the small size of canine bone segments. They can be implanted so that the mobility of the operated animal is maintained immediately after surgery. Advantageously, the bone plate system of this invention provides intimate contact between fractured bone segments during the healing period. A long-term permanent bond between the implant and the underlying bone structure is effected, and extended motion meeting the canine needs is achieved. Once implanted, the bone plate is not removed during the remaining lifetime of the dog. It is highly reliable in operation, and functions continuously in the implanted condition without corrosion or rejection reactions throughout its service life.

Generally stated, the multipurpose bone plate system of this invention comprises: a series of symmetrical bone plates having angulation and compression slots that enables easy bending of the bone plate. This symmetrical bone plate may be used for either the left side or the right side of an animal. A sterile malleable trial template in the shape of a bone plate made from annealed stainless steel, annealed copper, annealed aluminum, polymer sheet and the like is used to first create a bone plate template using the actual bone shape of the animal in surgery. This template is then removed from the actual bone of the animal in surgery, and inserted into an ergonomic bending and contouring tower. The bending and contouring tower has angulation slots and compression slots at various locations to bend a bone plate using angulation and compression tools. These angulation and compression slots of the bending and contouring tower are adjusted using the bone plate template, and set in accordance with its geometrical requirements. Bending and contouring a bone plate is accomplished by using specialized bending and contouring tools which work together with the angulation and compression slot of the bending and contouring tower, the positions of which have been set by using the bone plate template. The resulting three-dimensionally contoured bend plate surrounds the fractured bone of the animal in surgery due to the accurate bending and contouring thereof. Attachment of the three-dimensionally shaped bone plate to the fractured bone is accomplished by screws or nails driven through six apertures in the bone plate.

The System includes bone plates having a thickness of 2.7 mm and 3.5 mm with multiple compression and angulation slots for easy bending of the bone plate. The thicker plate is used for larger and heavier animals. The bone plate is three-dimensionally contoured in an easy to use bending and contouring tower and addresses the clinical needs of animals with various bone geometry using a single bone plate. Due to the symmetrical shape of the one plate, the bone plate may be used for the left or right side fractured bones. The multiple applications of the system include, but are not limited to, pelvic osteotomy, ilial shaft fracture, proximal tibial osteotomy, distal radial fracture and partial carpal athrodesis. The versatility of the system minimizes the need to inventory a wide selection of plates and pins in order to address the varied requirements of clinical cases.

The bone plate of the system is symmetrical, has a combination of angulation and compression slots, and can be bent into either left or right components. The multipurpose bone plate is manufactured from 316 LVM stainless steel—a standard material for surgical implants, which provides a high degree of effectiveness, as evidenced by its clinical history and laboratory testing data. Deviations from this standard can impact product strength, biocompatibility and corrosion resistance.

The method of using the multi-purpose bone plate system comprises the following steps: 1) the surgeon inserts the sterile malleable bone plate template to surround the fractured bone segment; 2) the malleable bone plate is deformed by fingers until it surrounds the fractured bone; 3) the bone plate template is removed from the fractured bone; 4) the three-dimensionally shaped bone plate template is inserted into the bending and contouring tower; 5) the angulation and compression slots of the contouring and bending tower are adjusted to match the three dimensional shape of the bone plate template by inserting alignment pins; 6) the bone plate template is removed from the bending and contouring tower; 7) a bone plate is inserted into the bending and contouring tower; 8) the bone plate is three-dimensionally shaped using bending irons and bend and twist adapters to create a shape that is the same as the bone plate template; 9) the bending and contouring tower is bent with the three-dimensionally shaped bone plate into a flash sterilizing unit; 10) the sterile three-dimensionally shaped bone plate is removed from the bending and contouring tower and the bone plate is incorporated on the fractured bone.

BRIEF DESCRIPTION OF DRAWINGS

The invention will be more fully understood and further advantages will become apparent when reference is had to the following detailed description and the accompanying drawings, in which.

DESCRIPTION OF THE PREFERRED EMBODIMENTS

The present invention provides a method and means bending bone plates in three dimensions to provide multi-dimensional support to fractured bone segments. Such multi-dimensional support facilitates retention of the surgeon-set position of the bones during the bone-healing period. Shaped bone plates provided in accordance with the present invention are especially suited for canine use. Such bone plates can accommodate the small size of canine bone segments. They can be implanted so that the mobility of the operated animal is maintained immediately after surgery. An intimate contact between fractured bone segments is provided during the healing period. A long-term, permanent bond between the implant and the underlying bone structure is achieved. This long-term, permanent bond affords extended motion, thereby meeting canine needs. Once implanted, the bone plate is not removed during the remaining lifetime of the dog. It is highly reliable in operation, and functions continuously in the implanted condition without corrosion or rejection reactions throughout its service life.

In traumas involving bone fractures and osteotomies, it is oftentimes necessary to re-orient alignment between bone segments. Bone plates and screws have been used for decades to obtain this result. Such bone plates and screws are used at the fracture/osteotomy site to stabilize the segments of bone and to allow the normal healing process to take place. Bone segment stabilization is critical to the healing process, as it prevents non-union caused by micro motion between the bone segments.

The bone plate and screws must achieve fixation to each bony segment and then must provide for compression at the fracture/osteotomy site. Because bones have complex outer geometries, many bone plates have been designed for different indications, and are provided with given designs in left and right configurations. Notwithstanding the seemingly wide array of bone plates found in the prior art, bending or contouring of bone plates is still required in order to better fit the exterior cortex of the bone over the fracture site. This bending is typically accomplished with bending irons that grab the ends of the plate, thereby allowing the surgeon to bend and twist the bone plate in various directions to fit the bone. Generally, two bending irons are provided. With one bending iron in each hand loosely holding the plate at either end, the plate is bent and/or twisted in an approximate manner based on the surgeon's visual interpretation of the outer geometry of the bone. This process can be time consuming and oftentimes involves a trial and error process with the plate being bent, trial fitted to the bone, bent again, and so forth, until an adequate fit is established.

The present invention provides a bone plate system having certain design objectives and advantages, which include:
1. a bone plate design capable of addressing several different clinical indications owing to its ability to be properly contoured through use of angulation or compression slots disposed at suitably designed locations;
2. a bone plate design capable of addressing both left and right bones because of its ability to be properly contoured;
3. sufficient sizes within the bone plate design for application with different size/weight animals;
4. means for accurately contouring the bone plates intraoperatively;
5. means for contouring the bone plates wherein less iterations are necessary in order to achieve an accurate fit to the bone; and
6. an improved bending tower that can be disassembled and contained within the standard flash autoclave pan (11"×7"×1.4"), thereby providing for immediate use of the instrument between cases (following flash autoclaving).

With the design objectives met, the system of the present invention comprises a versatile bone plate system that addresses a multitude of clinical indications within one plate system. The design of the bone plates, together with an accurate method of contouring them, permits it to be used in a wide variety of applications. Significantly, the system affords significant financial benefits to a veterinarian practice. Usually different plate designs, some of which are designed for left configurations and others of which are designed for right configurations, are needed to address clinical cases such as TPLO, TPO, iliac shaft fractures and certain bone fusion applications. Not only are these different designs needed for these different indications, but multiple bone plate sizes are also required within each design. A bone plate system having a basic bone plate design for addressing a relatively small number of bone sizes, and an accurate method for contouring the plates, enables the surgeon to address a given population of clinical cases with a far smaller bone plate inventory.

Bone plates are commonly used to anchor bone segments having a bone fracture therein. The bone plate is attached to the bones by means of a multitude of screws or nails, which hold the bone segments in contact with each other at the fracture location. Since the bone plate provides the mechanical stability and the ability to apply load to the bone, the normal functioning of the animal treated is made possible even during the time period within which the bone fracture joint is healing. The bone plate and screws may be surgically removed after the bone healing process is complete, or left within the animal body. In either case, the bone plate is within the animal for at least three months (a typical bone healing period) or longer.

Key requirements for a bone plate include, in combination: 1) the ability to be readily attached to fractured bone segments; 2) fastening capability adequate to attach the bone plate to the bone segments, i.e. an adequate number of provisions for fasteners; 3) mechanical bone plate strength adequate to withstand applied loading without excessive deformation at the bone fracture joint; 4) corrosion resistance adequate to withstand body fluids during the remaining lifetime of the animal; and 5) bio-compatibility adequate to prevent rejection reactions of the bone plate. When a bone plate is used during surgery, it must have a shape appropriate to provide support; yet possess sterility sufficient to prevent the possibility of infection.

The present invention provides a multipurpose bone plate system having a bone plate thickness from about 2.7 mm to 3.5 mm to match the requirements of differently sized dogs. The bone plates are inherently symmetrical, and the ergonomic bending tower comprising a component of the system enables exceedingly accurate bending of these bone plates to three-dimensional shapes that better fit the requirements of bone support. The three dimensionally shaped bone plates are inserted during surgery to provide improved support for fractured bones so that the fracture location is completely immobilized, enhancing opportunity for the fractured area to promote bone growth. During this healing period, the animal is not immobilized and continues normal activity due to the support provided by the three-dimensionally shaped bone plate.

The bone plate is inserted by the surgeon. It surrounds the fractured bone and stays within the animal body for a substantial time period, typically greater than three months. Accordingly, the bone plate should be biocompatible and should not result in rejection reactions. The bone plates are composed of 316 LVM stainless steel. Surgical implantability of this steel composition is well established. The 316 LVM stainless alloy steel exhibits high strength, biocompatibility and corrosion resistance.

The bending tower comprises a series of angulation and compression slots that are positioned to create appropriate twisting capability for shaping a bone plate to match differently sized and shaped animals. The surgeon first evaluates his shape requirements by creating a multidimensional template that fits the requirements of a particular bone being operated on. The template is inserted into the bending tower and the angulations and compression slots are set to match the multidimensional template. A symmetrical bone plate is then inserted into the bending tower, wherein it is bent and twisted, using bend and twist bars, to create a three dimensional shape that essentially matches the shape of the multidimensional template. Once the surgeon is satisfied with the shape of the bone plate, the three dimensionally shaped bone plate is inserted back into the bending tower and flash sterilized, together with screws or nails, in a standard flash autoclaving pan, the dimensions of which are typically about 11"×7" and 1.4". At this point, the bone plate is ready for insertion surrounding the fractured bone sections. This is where I stopped.

The multipurpose bone plate system of the present invention ("the System") is composed of (i) a series of symmetrical bone plates, wherein separate plates for left and right configurations, respectively, are not required; (ii) malleable trial plate templates; and (iii) an ergonomic bending tower which provides for accurate bending and contouring of the bone plates. The bone plates are designed to allow for bending in order to provide for both left and right applications; the bone plates are offered in several sizes in order to provide clinical applications in a multitude of areas. In order to improve the fit of the bone plate to the bone, malleable templates are provided in the shape of the bone plates. The templates can be contoured to the bone and then used as a template in order to appropriately contour the actual bone plate. The bending tower provides for a stable set-up in order to easily bend and/or twist a bone plate and also to provide for alignment checks. The ease and accuracy of the bending tower in combination with the malleable templates significantly reduces the iterative process to fit the plate to the bone. In addition, with these bending options and the design of the bone plates, a multitude of clinical applications can be addressed with one design. Applications with the bone plates in conjunction with the bending tower include TPLO (Tibial Plateau Leveling Osteotomy), TPO (Triple Pelvic Osteotomy), iliac shaft fractures, partial carpal arthrodesis, proximal tibial osteotomy, and distal radial fracture.

Figure 1A:
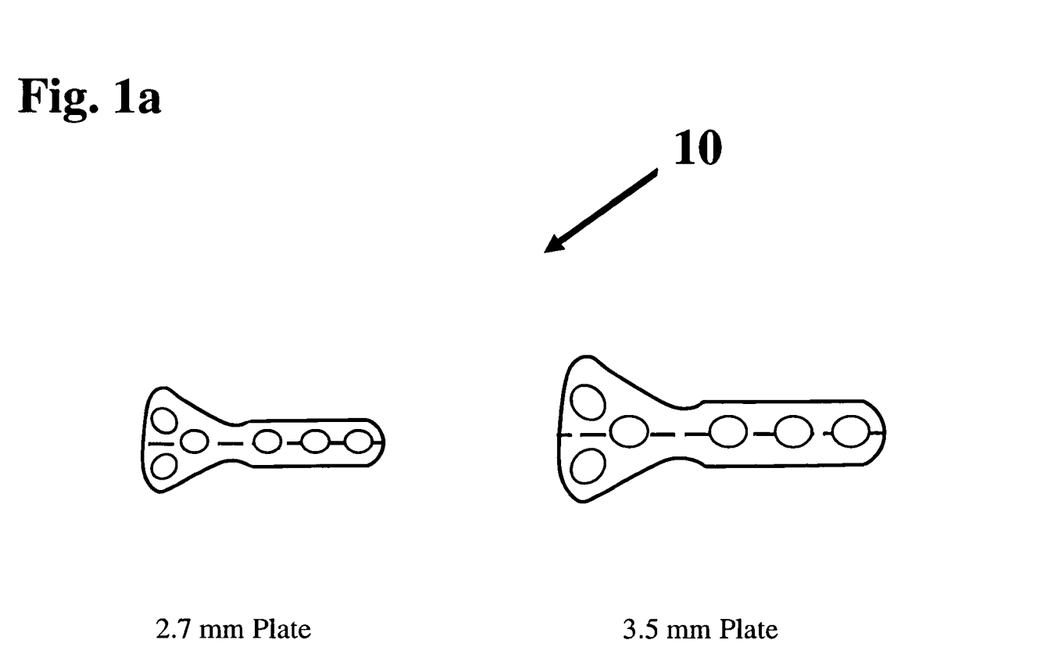
FIG. 1a is a photograph depicting two bone plates having a thickness of 2.7 mm and 3.5 mm.

FIG. 1a photograph illustrates at 10 two bone plates having a thickness of 2.7 mm and 3.5 mm with 3 holes or apertures in the right hand side and three holes or apertures on the left hand side for affixing the bone to sections of a broken bone. The bone plate is entirely symmetrical and in particular the left hand side of the bone plate has two lobes, which may be bent to accommodate a left hand or right hand bone section. Bending of this bone plate creates a three-dimensional bone plate that surrounds the broken bone, providing anchoring and stability. The bone plate is screwed-on or nailed-in using the six holes or apertures of the bone plate.

Figure 1B:
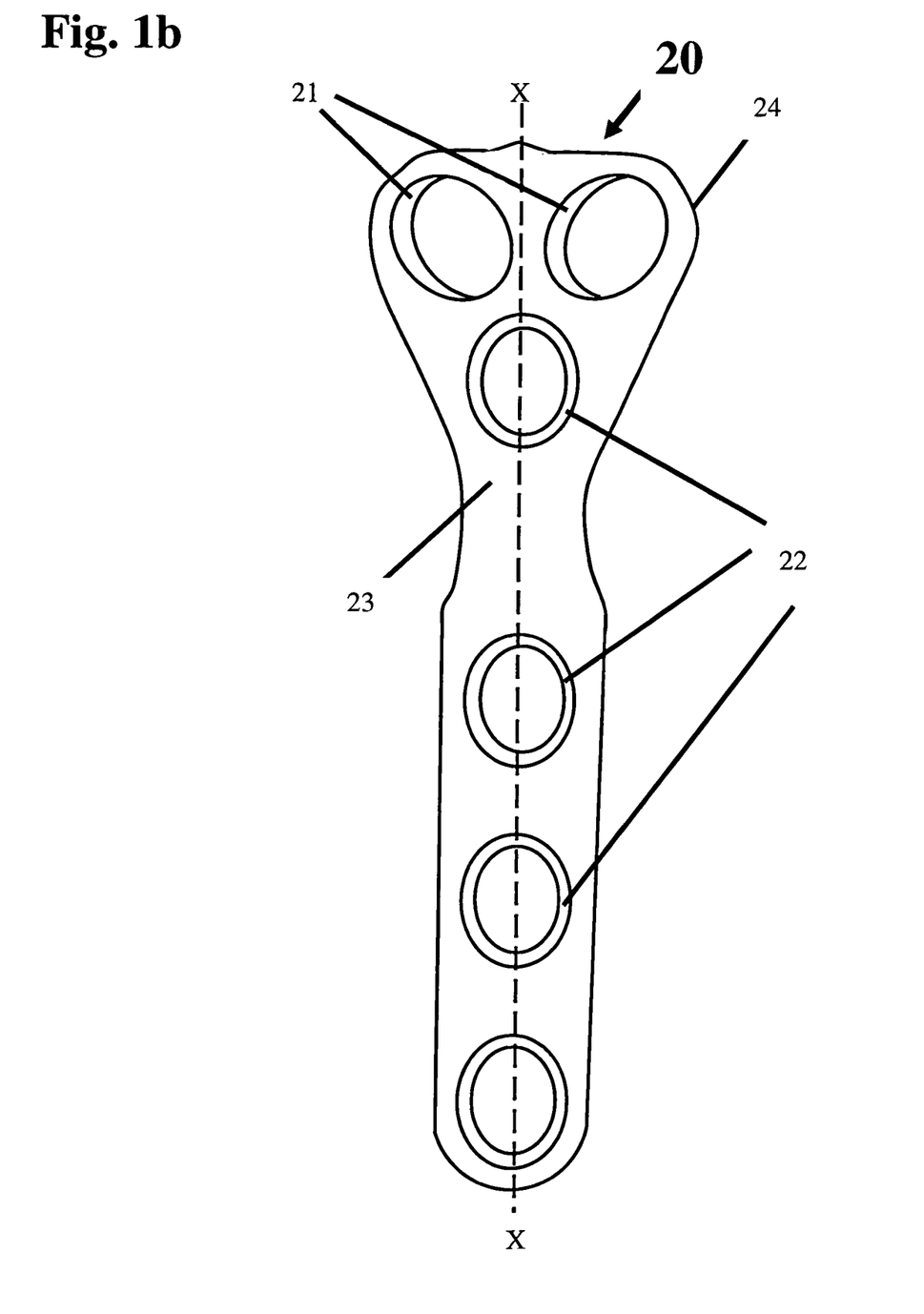
FIG. 1b is a photograph of a bone plate at a higher magnification illustrating the angulation slots and compression slots.

FIG. 1b illustrates at 20 the bone plate at a higher magnification. It shows six holes or apertures for accepting anchoring screws or nails and a number of slots placed at several strategic locations designed to permit easy bending or twisting of the bone plate. The angulation slots are shown at 21. The compression slots are shown at 22. The portion of the bone plate in the region 23 is narrowed to facilitate easy bending of the bone plate. The bone plate is made from 316 LVM stainless steel. The symmetrical lobe of the bone plate is shown at 24. The bone plate is bent along line XX to produce a three-dimensional shape. The presence of these slots allows the surgeon to bend the bone plate into a three dimensional shape that matches a bone that is being operated on.

Figure 2:
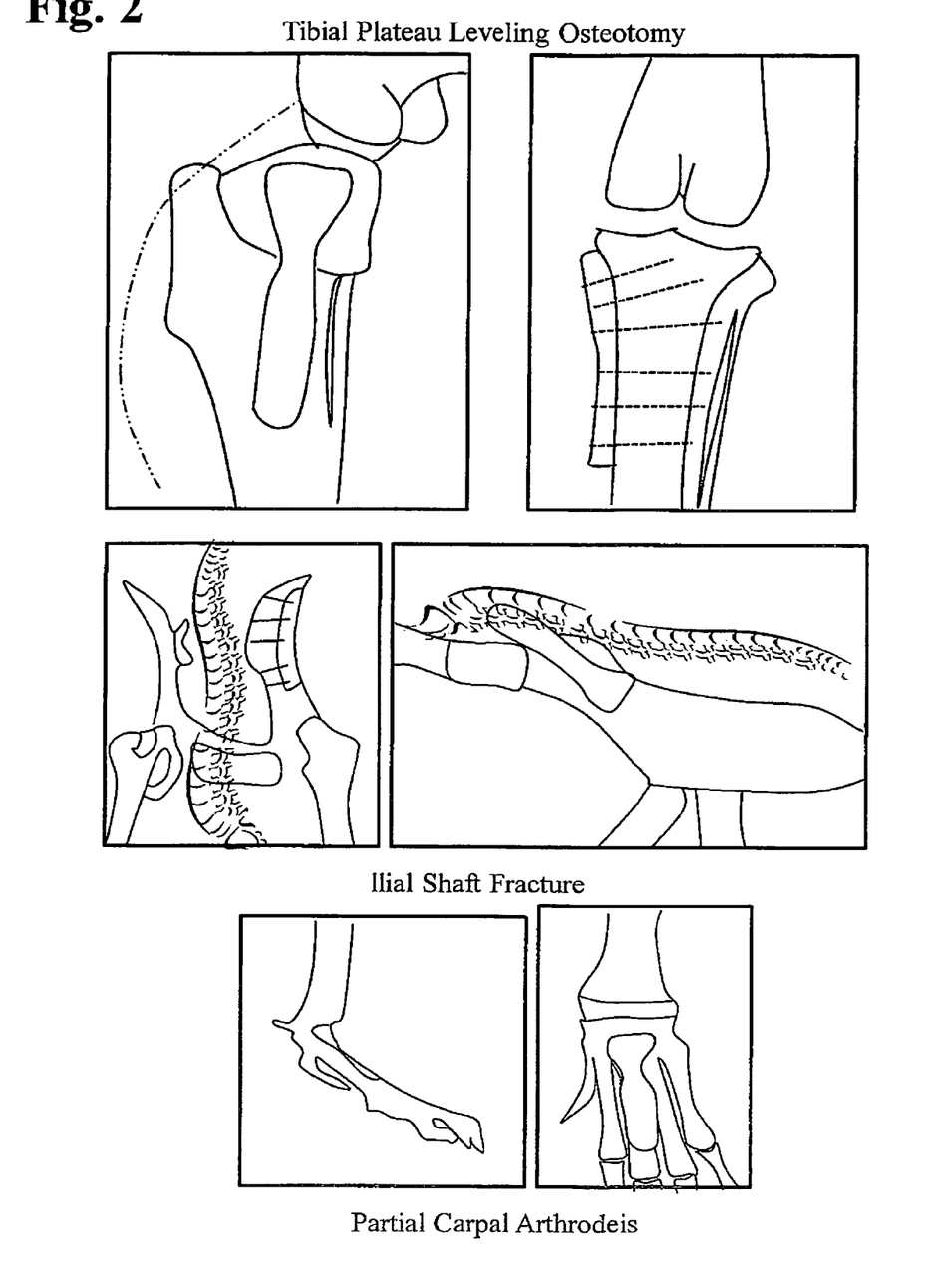
FIG. 2 illustrates radiographs of a bond fracture anchored with a bone plate and six screws.

FIG. 2 illustrates the radiographs of a bone fracture with bone plate anchored using six screws. The first radiograph shows two views of a tibial plateau leveling osteotomy. The second radiograph shows two views of an ilial shaft fracture mended by a bone plate. The third radiograph shows partial carpal arthrodeis. In all cases, the bone plate appears white since the stainless steel bone plate absorbs more of the x-rays as compared to the bone.

Figure 3A:
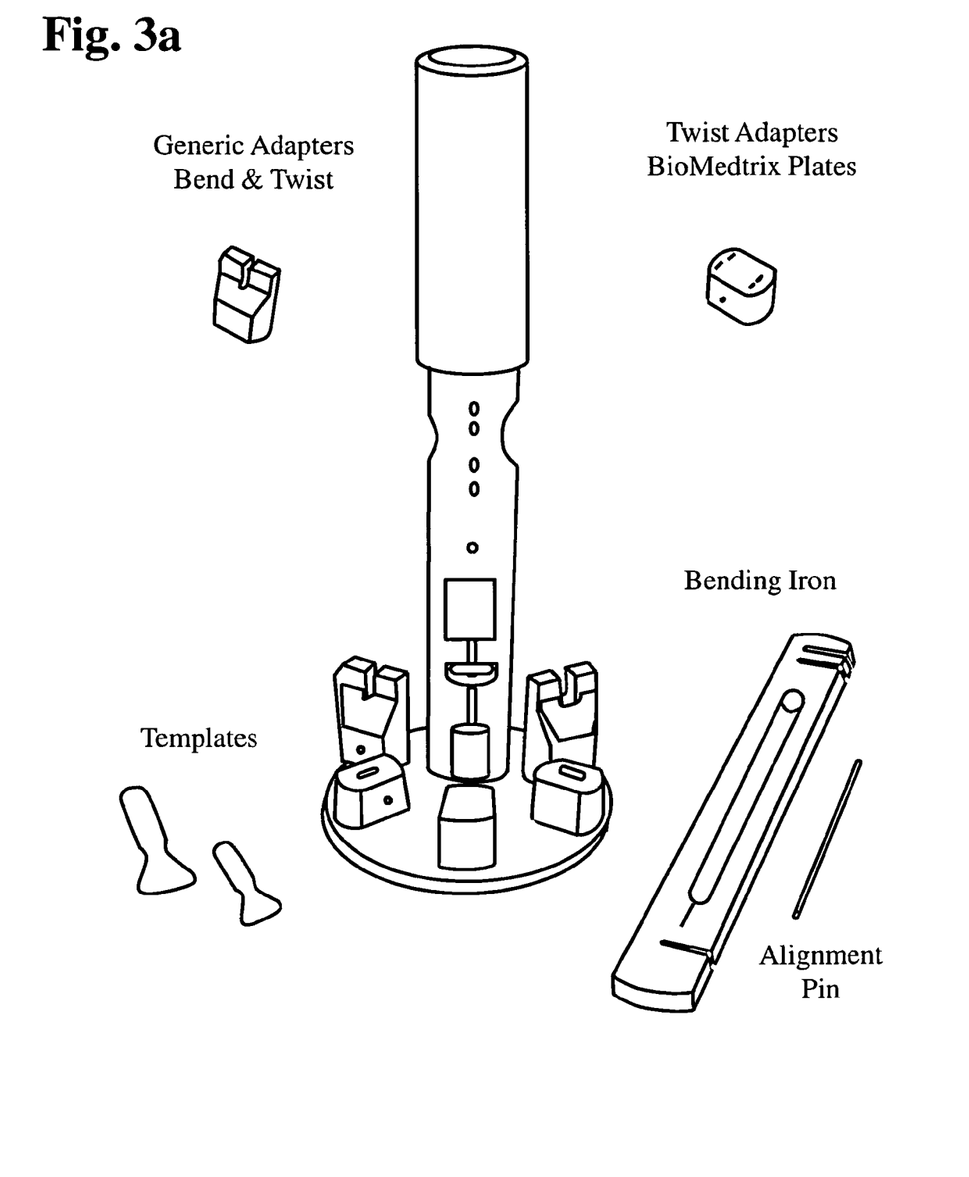
FIG. 3a illustrates a bending and contouring tower and its components.

FIG. 3a illustrates the bending and contouring tower, its components. The bending and contouring tower is provided with generic bending and twisting tools, a bending iron, alignment pins and a series of pliable templates. The surgeon bends the templates according to the shape of the bone plate desired. The alignment pins allow the setting of bending and twisting movements required to accomplish this multi-dimensional bone plate geometry. The twisting and bending slots in the bending and contouring tower are aligned according to the desired shape of the template. The bone plate is inserted into the bending and contouring tower and is bent using the bending iron and generic and twisting adapters.

Figure 3B:
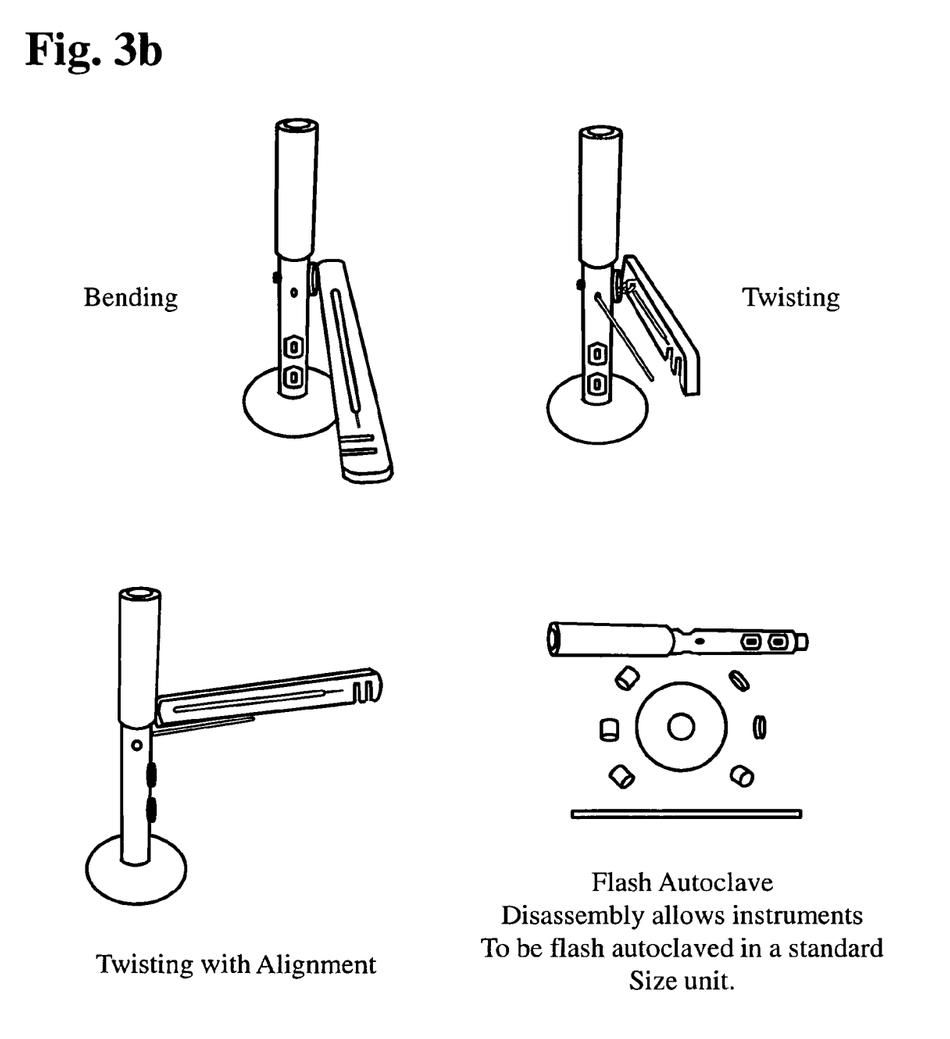
FIG. 3b illustrates the operation of the bending and twisting of a bone plate using the bending and contouring tower.

FIG. 3b illustrates the operation of bending and twisting of the bone plate using the bending and contouring tower. The slots present in the bone plate as illustrated in FIG. 1b make the bending and twisting possible.

The key features of the multi-purpose bone plate system are:
1. a bone plate design which can address several different clinical indications because of its ability to be properly contoured, matching the bone in three dimensions due to the presence of specially designed angulation or compression slots within the bone plate;
2. a bone plate design which can address both left and right bones because of its ability to be properly contoured;
3. sufficient sizes within the bone plate design for application with different size/weight animals;
4. means for accurately contouring the bone plates intraoperatively;
5. means for contouring the bone plates wherein less iterations are necessary in order to achieve an accurate fit to the bone; and
6. an improved bending tower that can be disassembled and contained within a standard flash autoclave pan (11"×7"×1.4"), thereby providing for immediate use of the instrument between cases (following flash autoclaving).

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A multi-purpose bone plate system, comprising:
   a. a symmetrical bone plate, bending and contouring tower and sterile malleable bone plate template;
   b. said sterile malleable bone plate template acquiring a three-dimensional shape of a fractured bone when deformed around an actual bone segment;
   c. said three-dimensionally shaped bone plate template positioned within the bending and contouring tower to set bending and contouring slot locations;
   d. said symmetrical bone plate having a right side and a left side separated by a narrowed arcuate region, wherein said left side of said bone plate has two conjoined symmetrical lobes without a gap/divot separating said lobes and being appointed to be bent to accommodate a left or right hand bone section and being provided with angulation and compression slots at selected locations and a central fold line to facilitate the three-dimensional shaping of the bone plate;
   e. said bone plate bent and twisted and contoured in said bending and contouring tower using angulation and compression slots and bending and twisting tools;
   f. said symmetrical bone plate being deformed by bending and twisting using said bending and contouring tower to a shape that replicates the three-dimensional shape of said bone plate template; and
   g. said symmetrical bone plate having six apertures to insert screws or nails to retain said three-dimensionally shaped bone plate against fractured bone segments;
   whereby said symmetrical bone plate is bent and twisted matching the three-dimensional shape of fractured bone providing complete support for left or right hand applications with minimal inventory of bond plates.

2. A multi-purpose bone plate system as recited by claim 1, wherein said symmetrical bone plate has a thickness of 2.7 mm.

3. A multi-purpose bone plate system as recited by claim 1, wherein said bone plate has a thickness of 3.5 mm.

4. A multi-purpose bone plate system as recited by claim 1, wherein said symmetrical bone plate is made from corrosion resistant high strength 316 LVM stainless steel.

5. A multi-purpose bone plate system as recited by claim 1, wherein said symmetrical bone plate has compression slots and angulation slots surrounding said apertures.

6. A multi-purpose bone plate system as recited by claim 1, wherein said sterile malleable bone plate template is made from annealed stainless steel sheet.

7. A multi-purpose bone plate system as recited by claim 1, wherein said sterile malleable bone plate template is made from annealed copper sheet.

8. A multi-purpose bone plate system as recited by claim 1, wherein said sterile malleable bone plate template is made from annealed aluminum sheet.

9. A multi-purpose bone plate system as recited by claim 1, wherein said sterile malleable bone plate template is made from polymeric sheet.

10. A multi-purpose bone plate system as recited by claim 1, wherein said sterile malleable bone plate template is three-dimensionally deformed by the surgeon to the exact shape of a fractured bone.

11. A multi-purpose bone plate system as recited by claim 10, wherein said three-dimensionally deformed sterile malleable bone plate template is used to set the compression slots and angulation slots of the bending and contouring tower by setting adjustable slot positions.

\* \* \* \* \*